US008781856B2

(12) United States Patent
Hanina et al.

(10) Patent No.: US 8,781,856 B2
(45) Date of Patent: *Jul. 15, 2014

(54) METHOD AND APPARATUS FOR VERIFICATION OF MEDICATION ADMINISTRATION ADHERENCE

(75) Inventors: Adam Hanina, New York, NY (US); Gordon Kessler, Mt. Kisco, NY (US)

(73) Assignee: Ai Cure Technologies LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/558,377

(22) Filed: Jul. 26, 2012

(65) Prior Publication Data

US 2012/0296666 A1 Nov. 22, 2012

Related U.S. Application Data

(63) Continuation of application No. 12/620,686, filed on Nov. 18, 2009, now abandoned.

(51) Int. Cl.
| | |
|---|---|
| *G06Q 50/00* | (2012.01) |
| *G06F 19/00* | (2011.01) |
| *G06Q 50/22* | (2012.01) |
| *G06K 9/00* | (2006.01) |

(52) U.S. Cl.
CPC ............ *G06F 19/3456* (2013.01); *G06Q 50/22* (2013.01); *G06K 9/00335* (2013.01)
USPC .................................. 705/2; 705/3; 382/107

(58) Field of Classification Search
CPC ............................ G06F 19/3456; G06Q 50/22
USPC ......................................................... 705/2–3
See application file for complete search history.

(56) References Cited

U.S. PATENT DOCUMENTS

| | | | |
|---|---|---|---|
| 3,814,845 A | 6/1974 | Hurlbrink et al. | |
| 5,065,447 A | 11/1991 | Barnsley et al. | |
| 5,441,047 A * | 8/1995 | David et al. .................. | 600/483 |
| 5,544,649 A | 8/1996 | David et al. | |
| 5,596,994 A * | 1/1997 | Bro ............................... | 600/545 |
| 5,619,991 A | 4/1997 | Sloane | |
| 5,646,912 A | 7/1997 | Cousin | |
| 5,752,621 A | 5/1998 | Passamante | |
| 5,764,296 A | 6/1998 | Shin | |
| 5,810,747 A | 9/1998 | Brudny et al. | |
| 5,911,132 A | 6/1999 | Sloane | |
| 5,961,446 A | 10/1999 | Beller et al. | |
| 5,963,136 A * | 10/1999 | O'Brien ..................... | 340/573.1 |

(Continued)

OTHER PUBLICATIONS

Wang et al. "Recent developments in human motion analysis." Pattern Recognition 36 (2003) 585-601.*

(Continued)

*Primary Examiner* — Neal Sereboff
*Assistant Examiner* — Anita Coupe
(74) *Attorney, Agent, or Firm* — Gordon Kessler

(57) ABSTRACT

A system and method of confirming administration of medication is provided. The method comprises the steps of receiving information identifying a particular medication prescription regimen, determining one or more procedures for administering such prescription regimen and identifying one or more activity sequences associated with such procedures. Activity sequences of actual administration of such prescription regimen are captured and then compared to the identified activity sequences to determine differences therebetween. A notice is provided if differences are determined.

27 Claims, 3 Drawing Sheets

(56) References Cited

U.S. PATENT DOCUMENTS

| | | | |
|---|---|---|---|
| 6,151,521 A | 11/2000 | Guo et al. | |
| 6,233,428 B1 | 5/2001 | Fryer | |
| 6,234,343 B1* | 5/2001 | Papp | 221/7 |
| 6,283,761 B1 | 9/2001 | Joao | |
| 6,380,858 B1 | 4/2002 | Yarin et al. | |
| 6,409,661 B1 | 6/2002 | Murphy | |
| 6,421,650 B1 | 7/2002 | Goetz et al. | |
| 6,483,993 B1 | 11/2002 | Misumi et al. | |
| 6,484,144 B2 | 11/2002 | Martin et al. | |
| 6,535,637 B1 | 3/2003 | Wootton et al. | |
| 6,611,206 B2 | 8/2003 | Eshelman et al. | |
| 6,628,835 B1* | 9/2003 | Brill et al. | 382/226 |
| 6,705,991 B2 | 3/2004 | Bardy | |
| 6,879,970 B2 | 4/2005 | Shiffman et al. | |
| 6,988,075 B1 | 1/2006 | Hacker | |
| 7,184,047 B1 | 2/2007 | Crampton | |
| 7,184,075 B2 | 2/2007 | Reiffel | |
| 7,256,708 B2 | 8/2007 | Rosenfeld et al. | |
| 7,277,752 B2 | 10/2007 | Matos | |
| 7,304,228 B2 | 12/2007 | Bryden et al. | |
| 7,307,543 B2 | 12/2007 | Rosenfeld et al. | |
| 7,317,967 B2 | 1/2008 | DiGianfilippo et al. | |
| 7,340,077 B2 | 3/2008 | Gokturk | |
| 7,395,214 B2 | 7/2008 | Shillingburg | |
| 7,415,447 B2 | 8/2008 | Shiffman et al. | |
| 7,448,544 B1 | 11/2008 | Louie et al. | |
| 7,562,121 B2 | 7/2009 | Berisford et al. | |
| 7,627,142 B2 | 12/2009 | Kurzweil et al. | |
| 7,657,443 B2 | 2/2010 | Crass et al. | |
| 7,692,625 B2 | 4/2010 | Morrison et al. | |
| 7,712,288 B2* | 5/2010 | Ramasubramanian et al. | 53/507 |
| 7,747,454 B2 | 6/2010 | Bartfeld et al. | |
| 7,761,311 B2 | 7/2010 | Clements et al. | |
| 7,769,465 B2 | 8/2010 | Matos | |
| 7,774,075 B2 | 8/2010 | Lin et al. | |
| 7,874,984 B2 | 1/2011 | Elsayed et al. | |
| 7,881,537 B2* | 2/2011 | Ma et al. | 382/190 |
| 7,908,155 B2 | 3/2011 | Fuerst et al. | |
| 7,912,733 B2 | 3/2011 | Clements et al. | |
| 7,945,450 B2* | 5/2011 | Strawder | 705/2 |
| 7,956,727 B2 | 6/2011 | Loncar | |
| 7,983,933 B2 | 7/2011 | Karkanias et al. | |
| 8,065,180 B2* | 11/2011 | Hufford et al. | 705/7.38 |
| 8,321,284 B2 | 11/2012 | Clements et al. | |
| 8,370,262 B2* | 2/2013 | Blessing | 705/64 |
| 8,606,595 B2* | 12/2013 | Udani | 705/2 |
| 2001/0049673 A1 | 12/2001 | Dulong et al. | |
| 2001/0056358 A1 | 12/2001 | Dulong et al. | |
| 2002/0026330 A1 | 2/2002 | Klein | |
| 2002/0093429 A1 | 7/2002 | Matsushita et al. | |
| 2002/0143563 A1* | 10/2002 | Hufford et al. | 705/1 |
| 2003/0036683 A1* | 2/2003 | Kehr et al. | 600/300 |
| 2003/0058341 A1* | 3/2003 | Brodsky et al. | 348/169 |
| 2003/0164172 A1 | 9/2003 | Chumas et al. | |
| 2003/0190076 A1 | 10/2003 | Delean | |
| 2003/0225325 A1 | 12/2003 | Kagermeier et al. | |
| 2004/0100572 A1 | 5/2004 | Kin | |
| 2004/0107116 A1 | 6/2004 | Brown | |
| 2004/0155780 A1* | 8/2004 | Rapchak | 340/573.1 |
| 2005/0144150 A1 | 6/2005 | Ramamurthy et al. | |
| 2005/0149361 A1 | 7/2005 | Saus et al. | |
| 2005/0180610 A1 | 8/2005 | Kato et al. | |
| 2005/0182664 A1 | 8/2005 | Abraham-Fuchs et al. | |
| 2005/0234381 A1 | 10/2005 | Niemetz et al. | |
| 2005/0267356 A1 | 12/2005 | Ramasubramanian et al. | |
| 2006/0066584 A1 | 3/2006 | Barkan | |
| 2006/0218011 A1 | 9/2006 | Walker et al. | |
| 2006/0238549 A1 | 10/2006 | Marks | |
| 2006/0294108 A1* | 12/2006 | Adelson et al. | 707/10 |
| 2007/0008112 A1 | 1/2007 | Covannon et al. | |
| 2007/0008113 A1 | 1/2007 | Spoonhower et al. | |
| 2007/0030363 A1 | 2/2007 | Cheatle et al. | |
| 2007/0118389 A1 | 5/2007 | Shipon | |
| 2007/0194034 A1 | 8/2007 | Vasiadis | |
| 2007/0233035 A1 | 10/2007 | Wehba et al. | |
| 2007/0233049 A1 | 10/2007 | Wehba et al. | |
| 2007/0233050 A1 | 10/2007 | Wehba et al. | |
| 2007/0233281 A1 | 10/2007 | Wehba et al. | |
| 2007/0233520 A1 | 10/2007 | Wehba et al. | |
| 2007/0233521 A1 | 10/2007 | Wehba et al. | |
| 2007/0273504 A1 | 11/2007 | Tran | |
| 2007/0288266 A1* | 12/2007 | Sysko et al. | 705/2 |
| 2008/0000979 A1 | 1/2008 | Poisner | |
| 2008/0093447 A1 | 4/2008 | Johnson et al. | |
| 2008/0114226 A1 | 5/2008 | Music et al. | |
| 2008/0114490 A1 | 5/2008 | Jean-Pierre | |
| 2008/0119958 A1* | 5/2008 | Bear et al. | 700/244 |
| 2008/0138604 A1 | 6/2008 | Kenney et al. | |
| 2008/0140444 A1 | 6/2008 | Karkanias et al. | |
| 2008/0162192 A1 | 7/2008 | Vonk et al. | |
| 2008/0172253 A1* | 7/2008 | Chung et al. | 705/3 |
| 2008/0178126 A1 | 7/2008 | Beeck et al. | |
| 2008/0201174 A1 | 8/2008 | Ramasubramanian et al. | |
| 2008/0219493 A1 | 9/2008 | Tadmor | |
| 2008/0275738 A1 | 11/2008 | Shillingburg | |
| 2008/0290168 A1 | 11/2008 | Sullivan et al. | |
| 2008/0297589 A1 | 12/2008 | Kurtz et al. | |
| 2008/0303638 A1 | 12/2008 | Nguyen et al. | |
| 2009/0012818 A1* | 1/2009 | Rodgers | 705/3 |
| 2009/0018867 A1 | 1/2009 | Reiner | |
| 2009/0043610 A1 | 2/2009 | Nadas et al. | |
| 2009/0048871 A1 | 2/2009 | Skomra | |
| 2009/0095837 A1 | 4/2009 | Lindgren | |
| 2009/0128330 A1 | 5/2009 | Monroe | |
| 2009/0159714 A1 | 6/2009 | Coyne, III et al. | |
| 2009/0217194 A1 | 8/2009 | Martin et al. | |
| 2009/0245655 A1 | 10/2009 | Matsuzaka | |
| 2010/0042430 A1* | 2/2010 | Bartfeld | 705/2 |
| 2010/0050134 A1 | 2/2010 | Clarkson | |
| 2010/0057646 A1 | 3/2010 | Martin et al. | |
| 2010/0092093 A1 | 4/2010 | Akatsuka et al. | |
| 2010/0136509 A1 | 6/2010 | Mejer et al. | |
| 2010/0138154 A1 | 6/2010 | Kon | |
| 2010/0255598 A1 | 10/2010 | Melker | |
| 2010/0262436 A1 | 10/2010 | Chen et al. | |
| 2010/0316979 A1 | 12/2010 | Von Bismarck | |
| 2011/0021952 A1 | 1/2011 | Vallone | |
| 2011/0119073 A1 | 5/2011 | Hanina et al. | |
| 2011/0153360 A1 | 6/2011 | Haninia et al. | |
| 2011/0161109 A1 | 6/2011 | Pinsonneault et al. | |
| 2011/0195520 A1 | 8/2011 | Leider et al. | |
| 2011/0275051 A1 | 11/2011 | Hanina et al. | |
| 2012/0011575 A1* | 1/2012 | Cheswick et al. | 726/5 |
| 2012/0075464 A1 | 3/2012 | Derenne et al. | |
| 2012/0081551 A1* | 4/2012 | Mizuno et al. | 348/150 |
| 2012/0140068 A1* | 6/2012 | Monroe et al. | 348/143 |
| 2012/0182380 A1* | 7/2012 | Ohmae et al. | 348/14.03 |

OTHER PUBLICATIONS

Ammouri, S.; Bilodeau, G.-A, "Face and Hands Detection and Tracking Applied to the Monitoring of Medication Intake," Computer and Robot Vision, 2008. CRV '08. Canadian Conference on, vol., no., pp. 147,154, May 28-30, 2008.*

Batz, et al. "A computer vision system for monitoring medication intake," in Proc. IEEE 2nd Canadian Conf. on Computer and Robot Vision, Victoria, BC, Canada, 2005, pp. 362-369.*

Valin, et al. "Video Surveillance of Medication Intake", Int. Conf. of the IEEE Engineering in Medicine and Biology Society, New York City, USA, Aug. 2006.*

V.F.S. Fook et al. "Smart Mote-Based Medical System for Monitoring and Handling Medication Among Persons with Dementia." ICOST 2007, LNCS 4541, pp. 54-62, 2007.*

PR Newswire. "Pilot Study Using Video Cell Phones for Mobile Direct Observation (MDOT) to Monitor Medication Compliance of TB Patients." New York: Mar. 23, 2009.*

Danya International, Inc., *Pilot Study Using Cell Phones for Mobile Direct Observation Treatment to Monitor Medication Compliance of TB Patients*, Mar. 20, 2009, www.danya.com/MDOT.asp.

University of Texas, *GuideView*, Mar. 15, 2007, http://www.sahs.uth.tmc.edu/MSriram/GuideView/.

Chen, Pauline W., *Texting as a Health Tool for Teenagers*, The New York Times, Nov. 5, 2009, http://www.nytimes.com/2009/11/05/health/05chen.html?_r=1&emc=.

(56) References Cited

OTHER PUBLICATIONS

Whitecup, Morris S., *2008 Patient Adherence Update: New Approaches for Success*, Guideline Trend Report, Oct. 2008.
Osterberg, Lars and Blaschke, Terrence, *Adherence to Medication*, New England Journal of Medicine 2005; 353:487-97, Aug. 4, 2005.
"Global Tuberculosis Control: A short update to the 2009 report", *World Health Organization*, (2009).
"Super-Resolution", *Wikipedia*, (Oct. 5, 2010).
Non-Final Office Action from PTO, Cited in U.S. Appl. No. 12/620,686, (Dec. 21, 2011),1-78.
Final Office Action from PTO, Cited in U.S. Appl. No. 12/620,686, (May 8, 2012), 1-24.
PCT Search report and written opinion, Cited in (PCT/US2010/56935, (Jan. 12, 2011),1-9.
International Preliminary Report on Patentability, cited in (PCT/US2010/056935) (May 31, 2012), 1-8.
Non-Final Office Action from PTO, Cited in U.S. Appl. No. 12/646,383, (Dec. 22, 2011),1-78.
Final Office Action from PTO, Cited in U.S. Appl. No. 12/646,383, (May 8, 2012), 1-31.
Non-Final Office Action from PTO, Cited in U.S. Appl. No. 12/646,603, (Oct. 13, 2011),1-74.
Final Office Action from PTO, Cited in U.S. Appl. No. 12/646,603, (Feb. 1, 2012), 1-17.
Non Final Office Action from PTO, Cited in U.S. Appl. No. 12/728,721, (Jan. 6, 2012), 1-31.
Final Office Action from PTO, Cited in U.S. Appl. No. 12/728,721, (Apr. 12, 2012), 1-31.
Non-Final Office Action from PTO, Cited in U.S. Appl. No. 12/815,037, (Mar. 28, 2012),1-17.
PCT Search report and written opinion, Cited in (PCT/US2011/35093 (Sep. 12, 2011),1-8.
Non-Final Office Action from PTO, Cited in U.S. Appl. No. 12/898,338, (Jun. 19, 2012), 1-16.
PCT Search report and written opinion, Cited in (PCT/US12/41785, (Aug. 17, 2012),1-10.
PCT Search report and written opinion, Cited in (PCT/US12/42843), (Aug. 31, 2012),1-8.
Non-Final Office Action from PTO, Cited in U.S. Appl. No. 13/558,380, (Oct. 4, 2012), 1-20.
Final Office Action from PTO, Cited in U.S. Appl. No. 12/815,037, (Sep. 13, 2012), 1-15.
Non-Final Office Action from PTO Cited in U.S. Appl. No. 12/899,510, (Jan. 23, 2013), 1-20.
PCT Search report and written opinion, Cited in (PCT/US11/54666), (Feb. 28, 2012), 1-13.
Final Office Action from PTO, Cited in U.S. Appl. No. 12/898,338, (Nov. 9, 2012), 1-12.
PCT Search report and written opinion, Cited in (PCT/US11/54668), Feb. 28, 2012, 1-12.
Non-Final Office Action from PTO, Cited in U.S. Appl. No. 13/189,518, (Dec. 21, 2012), 1-10.
PCT Search report and written opinion, Cited in (PCT/US12/42843), (Aug. 31, 2012) 1-8.
PCT Search report and written opinion, Cited in (PCT/US2012/051554), (Oct. 19, 2012), 1-12.
Huynh et al., Real time detection, tracking and recognition of medication intake. World Academy of Science, Engineering and Technology 60 (2009), 280-287.
PCT Search report and written opinion, Cited in (PCT/US12/59139), (Dec. 18, 2012), 1-15.
Final Office Action from PTO, Cited in U.S. Appl. No. 13/588,380, (Mar. 1, 2013), 1-27.
Non-Final Office Action from PTO Cited in U.S. Appl. No. 12/646,603, (Jun. 13, 2013), 1-16.
Non-Final Office Action from PTO Cited in U.S. Appl. No. 12/728,721, (May 9, 2013), 1-25.
Non-Final Office Action from PTO, Cited in U.S. Appl. No. 12/815,037, (Jul. 18, 2013), 1-19.
Final Office Action from PTO Cited in U.S. Appl. No. 12/899,510, (Aug. 28, 2013).
Final Office Action from PTO, Cited in U.S. Appl. No. 13/189,518, (Jul. 23, 2013), 1-16.
Non-Final Office Action from PTO Cited in U.S. Appl. No. 13/235,387, Sep. 12, 2013), 1-16.
PCT Search report and written Opinion, Cited in (PCT/US13/20026), (Aug. 5, 2013), 1-14.
Bilodeau et al. Monitoring of Medication Intake Using a Camera System. Journal of Medical Systems 2011. [retrieved on Feb. 18, 2013] Retrieved from ProQuest Technology Collection.
Mintchell, "Exploring the Limits of Machine Vision", Automating World, Oct. 1, 2011.

\* cited by examiner

METHOD AND APPARATUS FOR VERIFICATION OF MEDICATION ADMINISTRATION ADHERENCE

CROSS REFERENCE TO RELATED APPLICATIONS

This application in a continuation of U.S. patent application Ser. No. 12/620,686, filed Nov. 18, 2009 to Hanina et al., entitled "Method and Apparatus for Verification of Medication Administration Adherence", currently pending, the entire contents thereof being incorporated herein by reference.

BACKGROUND OF THE INVENTION

It has been widely recognized that methods and systems for insuring proper medication ingestion by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is part of the problem. Also, the inability to confirm a proper prescription regimen being provided to a user in the first place may cause a number of other problems with the use of such medication. While other systems have been proposed to ensure such proper usage of medication, it is only the present invention that provides a complete solution to the medication management problem.

Dr Lars Osterberg, M.D. and Dr. Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in even clinical trials is "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series,* 2008 *Patient Adherence Update: New Approaches for Success*, October 2008, report similar discouraging statistics. It is against this backdrop of poor adherence, and potential danger to patients, that the present invention operates.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking The system may also provide a method for monitoring compliance of the patient with such a regimen, through the dispensing of medicine in accordance with a predetermined treatment protocol. While such a system provides many improvements for easing a burden on the patient, this system suffers in many ways.

Most importantly, this system provides no mechanism for actually confirming that a patient is in fact ingesting or otherwise properly administering required medication. While the system may be sufficient for one who is in full possession of their mental faculties, any individual who may have difficulty following directions, or one who is actively avoiding medication may still not be taking required medication after it is dispensed. Furthermore, the system requires preloading of various medications into a dispenser, and thus likely requires regular visits by an administering manager to be sure appropriate medications are in fact loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or the relationship of adherence to the efficacy of the drug over time. When customizing a medication regimen or monitoring a personal medication regimen, this is particularly relevant.

Additionally, existing systems fail to maintain an audit trail for post administration review by a medical official, and further cannot therefore confirm confirmation of proper medication administration. Existing systems are further generally impractical in that they fail to address many of a patient's other healthcare needs, including billing, insurance paperwork and filing, education regarding healthy living and proper use of medications, easing obtaining refills for medications, and providing feedback to a medical service provider, for example, in advance of an appointment so that the medical provider can be prepared for such an appointment.

Therefore, it would be desirable to provide a method and apparatus that overcomes the drawbacks of the prior art.

SUMMARY OF THE INVENTION

In accordance with the present invention, a system and method are provided that allow for complete control and verification of adherence to a prescribed medication protocol, whether is a health care provider's care, or when self administered in a homecare situation by a patient. The system and method preferably includes a means for receiving user medication information, including a medication profile and history, providing indications to a user regarding when to take a medication, and which medication to take, imaging medication either in pill or container form to confirm a correct medication is being taken, confirming, in accordance with the user medication history that a new medication will not conflict with an already being taken medication (including nonprescription medication that may be used by a patient), scan a group of medication containers or pills to inform a user which is the correct medication through the use of visual, verbal or other prompts, providing assistance information to aid a user in properly taking the medication, imaging, employing still photos, video sequences or other activity or gesture recognition techniques, the user to confirm that the medication is being actually and properly taken, providing any appropriate additional or special instructions, using the imaging to note any possible adverse effects associated with taking of the medication, accumulating statistics about adherence to a prescribed protocol, assisting in reordering medication on an as-needed basis and notifying a medical professional if the user is not properly following a prescribed protocol.

From beginning to end, a user is provided with a system and method that aids the user in properly following a protocol, while informing an administrator of any deviations from the protocol, either innocent or purposeful, by a user so that an early interaction may be provided. The present invention is the only medication adherence verification system that may determine whether a user is actually following a protocol, and provide additional assistance to a user, starting with instructions, video instructions, and the like, and moving up to contact from a medication administrator through phone, email video conferencing or the like, if it is determined that the user may benefit from such assistance. Upon prescription of a medication to a user and entry of appropriate medical information into the system, the pharmacist or other medical personnel may allow the system to image the medication or enter medication information in any number of ways, thus recalling one or more preferred protocols for administration of the medication. An image of the medication may be further provided to the pharmacist upon this or any subsequent refills of the medication and act as an added visual check to confirm proper medication administration. The personnel may then select a desired protocol, thus removing a likely point of error, incorrect instructions to a user. Further, a medication image may be shown to a patient when they are to take a medication, to thus further ensure proper medication is administered.

Further in accordance with the invention, access to such medication information may be made available to emergency responders, hospital or other medical service providers or the like. It is contemplated that such information may be available by entering a predefined sequence into a patient's cellular telephone, other mobile device, or home based system. Further access may be provided at a predetermined website or the like.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

In accordance with the invention, a system and process are provided that improve adherence to medical protocol, and give administrators a tangible and concrete manner in which to confirm compliance or lack thereof, and the ability to intervene early in the process to ensure that patients are properly taking their medication. The system and method of the invention provide for prescription selection, instructions to patients on the use of any prescription medications, and verification to a doctor or other service provider of patient adherence to the prescribed protocol.

Figure 1:
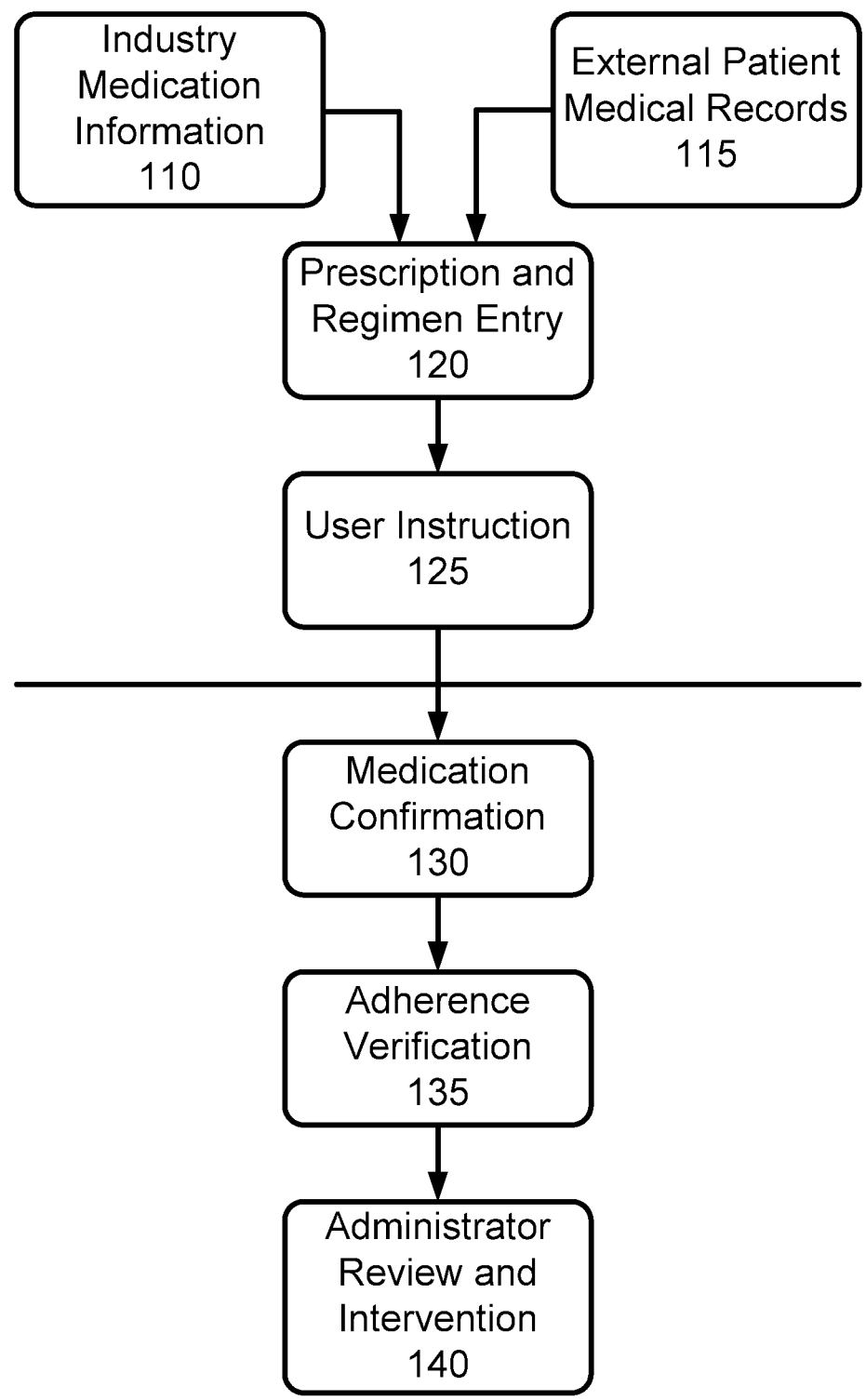
FIG. 1 is a flow chart diagram depicting top level functionality in accordance with an embodiment of the present invention.

Referring first to FIG. 1, a data flow overview is shown. In accordance with the invention, existing industry medication information databases 110 are employed to access prescription, interaction, application and other available information about any number of proposed prescription and non-prescription medications. Further, patient medical records 115 are used, and as will be described below, are used in conjunction with the industry medical information and a medical professional's prescribing expertise to prescribe a medicine regimen, and enter such a regimen into the system of the invention at 120. Once entered into the system, a particular prescription regimen causes a set of user instructions 125 to be generated. Such user instructions may include general instructions about a particular medication, methods for ingestion, concerns about side effects, concerns about drug interactions with common substances or medications, or other medications prescribed to the patient by the system or by another medical service provider. It is contemplated in accordance with the invention that such set of user instructions may be interactive, allowing a user to view additional information about such instructions or prescriptions as desired. These instructions may comprise written, audio or video instructions. Furthermore, it is contemplated in accordance with the invention that at various points during the instruction set, for example when a patient asks a particular type of question, or asks to receive additional information about a particular aspect of the medication or prescription regimen, that the system may reach out and contact a representative of a medical service provider to provide the patient with additional, personal help as necessary, if it is determined that such intervention by the medical professional would be desirable to the patient. Thus, such a patient may be assisted in properly taking medication so that various errors do not take place. Indeed, in more traditional scenarios, it is only after perhaps finishing a prescription regimen and a return to a doctor that it is discovered that the medication may have been taken incorrectly. In accordance with the present invention, early intervention with such issues can be exercised to deter any possible unfortunate outcomes from improper administration of medication. It is contemplated in accordance with the invention that a medical service provide or one of the individuals noted above be provided with a patient dashboard for managing prescription regimes for one or more patients. Such a dashboard allows the medical professional to monitor any number of patients in a manner that will be described below, allow statistical analyses of patient adherence and other patient reactions, provide links to information, including recorded activity sequences for one or more patients, and generally allow the medical professional to monitor and administer medication to all of their patients form a convenient single access point. Such a dashboard also allows for monitoring of any health care providers that may be administering medication to a number of patients, or review of one or more administration sequences or the like.

Additionally, it is contemplated in accordance with the invention that the patient be provided with a user interface dashboard or the like allowing of modification of prescription regimen and instruction information by the patient. Thus, by way of example, if a user is to take a particular medication before eating in the morning, the user may be able to determine when a reminder for such medication will be given. If the patient is an early riser, the reminder may be provided by cell phone or email at 6:00 AM. Conversely, if the patient sleeps late and normally does not eat an early meal, reminders can be set for later in the morning, thus matching a patient's schedule. Of course, any such patient adjustments must be set within broader prescription regimen as defined by the prescribing medical provider. It is contemplated in accordance with the invention that a touch or other user friendly graphical user interface be provided so that the user can easily manipulate any number of prescription factors, and perhaps enter additional information that may be useful to a prescribing medical provider, such as level of fatigue, level of hunger, jitter inducing medications, etc. All of these data collection points allow for a smoother administration of medication to a patient, and therefore a more likely chance of adherence to a prescribed protocol.

Referring to the portion of FIG. 1, the horizontal line indicates a time for patient ingestion or other administration of medication. In accordance with the invention, confirmation of patient adherence to the prescribed administration schedule for the medication is determined. While such confirmation may take a number of forms, in accordance with the invention, a preferred method for such confirmation may include capturing a video sequence of the patient actually administering the medication. In a further preferred method, such a sequence for such confirmation may include employing a facial recognition sequence or other biometric confirmation that a particular patient is in fact receiving treatment. Activity recognition, gesture recognition or other feature for determining whether a particular subject movement meets a predefined movement sequence may be employed to be sure that the patient is properly taking prescribed medication. The patient may then display a medication container and/or an actual pill or other medication form to an imaging apparatus, and the apparatus confirming that the medication is correct and is the currently prescribed medication to be taken through the user of text recognition, pill recognition, or other appropriate medication recognition scheme. This sequence of steps therefore acts as an audit trail each time a medication is taken, that can be reviewed later, to ensure that a patient is properly following a regimen.

Furthermore, in accordance with the present invention, a video image of the patient actually administering or ingesting the medication may be taken and stored so that actual confirmation may be achieved, rather than simply relying on the patient to state that a particular medication was administered. Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. Finally, in accordance with the invention, if recording of a video of a patient having the medication administered thereto is not possible, the system of the invention will recognize such an issue and request audio confirmation as a next best option. If the audio confirmation is also not possible, then a less reliable method of confirmation, such as a keyboard confirmation by the patient may be accepted. If higher reliability methods of confirmation are not available for an extended period of time, an alarm is preferably forwarded to a medical professional to inquire as to reasons and to remedy any situation that might be wrong in the administration situation.

These steps of confirming identity, confirming medication and confirming administration are then reviewed to verify adherence to the prescribed protocol at 135. Such review is preferably performed automatically by a computing system that is able to align the actual recorded images with ideal or expected images, or through the user of other activity or gesture recognition as mentioned above. In the case of facial recognition and bottle or pill recognition, such techniques are known in the art. With regard to video confirmation of adherence to prescribed medicine administration procedures, such processing may include various stick figure comparison analyses, motion recognition analysis, or other schemes as noted above able to determine whether appropriate actions have been performed by the patient.

The ability to provide automated determination of adherence to proper administration procedures allows for a large number of such images to be review in a short period of time. Even if actual and complete lack of adherence is not able to be determined 100% in each possible situation, the ability to pre screen the administration video captures to remove from further consideration administration situations that are clearly compliant may reduce a number of compliance situations to be reviewed substantially by a medical professional substantially.

In an additional embodiment of the invention the imaged sequences used for activity recognition to determine regimen adherence may be further used to check for adverse or other reactions to taking of the medication. Thus, in addition to simply determining proper adherence to a protocol, such activity or gesture recognition may determine any number of different actions that may have been taken by a patient. Thus, actions taken before medication administration, or actions taken after medication administration may give insight into reasons for particular responses, etc. Thus, before administration, in accordance with the invention, activity recognition may determine a current activity of a user. Any subsequent reminders to take a medication may in part be based upon this determined activity. By way of example, if a user is putting on a coat, or is determined to be leaving a residence or other facility or the like, a reminder to take a medication before leaving may be provided, even if earlier than normal, or if medication is portable, the user may be reminded to take the medication with them, and then subsequently reminded to administer the medication via notification on a mobile device. By way of further example, if the user is cooking, a reminder may be given to take the medication a predetermined time before eating. Other scenarios may be possible, thus allowing greater response from the system to ensure proper medication administration by a patient. Additionally, various patient consent issues may be prompted and recorded in accordance with the invention. Patients may ask further additional questions regarding such consent, thus insuring that patients have all of the information they need to make informed consent decisions, and medication providers have proper evidence of such consent.

Similarly, actions after taking medication may give insight into patient responses. Notice of fainting, falling down, lack of motion, facial gestures, gastrointestinal distress or the like may all be logged as adverse reactions to a particular medication regimen, and may allow for adjustment of dosage or prescription instructions in the future for the patient. If adverse reactions are severe, an immediate medication review and contact from a medical professional may be provided to cure the issue. Additionally, the system in accordance with the present invention may be directly tied and be interoperable with a pharmacy or medical provider's systems, thus allowing such recommendations for dosage changes, regimen changes and the like to be forwarded to these professionals automatically. Through such links, reordering medication, dosage changes, medication changes and the like may be automatically provided. Furthermore, ease of providing additional prescriptions can be enhanced as patient, medication and regimen information will already be available to the pharmacist or medical service provider.

After such automatic, or combination of automatic and manual, adherence verification is performed allowing a health care provider or other medical professional to review and verify results of the automatic comparison or direct review of captured activity sequences, and indication of variation from a desired identity, medication or application procedure may request administrator review of the situation, and intervention as may be determined necessary at 140. Such review may be required immediately as an emergency situation may exist, or such review may be less urgent, perhaps requiring an electronic communication with suggestions or the like from such an administrator or the like. Additionally, such adherence review may be stored over time for a particular patient, thus allowing for various medication trends to be determined, such as if a patient misses medication at a same time each week, or an indication that one particular health care worker aiding the patient may occasionally give an incorrect medication dosage amount. Thus, in addition to allowing for immediate notice of problems in medication administration, an audit trail for tracking the actions of various health care providers is generated.

Therefore, in accordance with the invention as set forth in FIG. 1, a method and system are provided in which patient adherence to a prescribed medication regimen can be reviewed, acutely for a particular instance, or over time to determine any changes in behavior of a patient. Because all aspects of such adherence are monitored preferably visually, and do not rely on patient confirmation of medication administration, desires of the patient are taken out of the equation, and a true review of actually procedures used in the medication administration can be studied.

Figure 2:
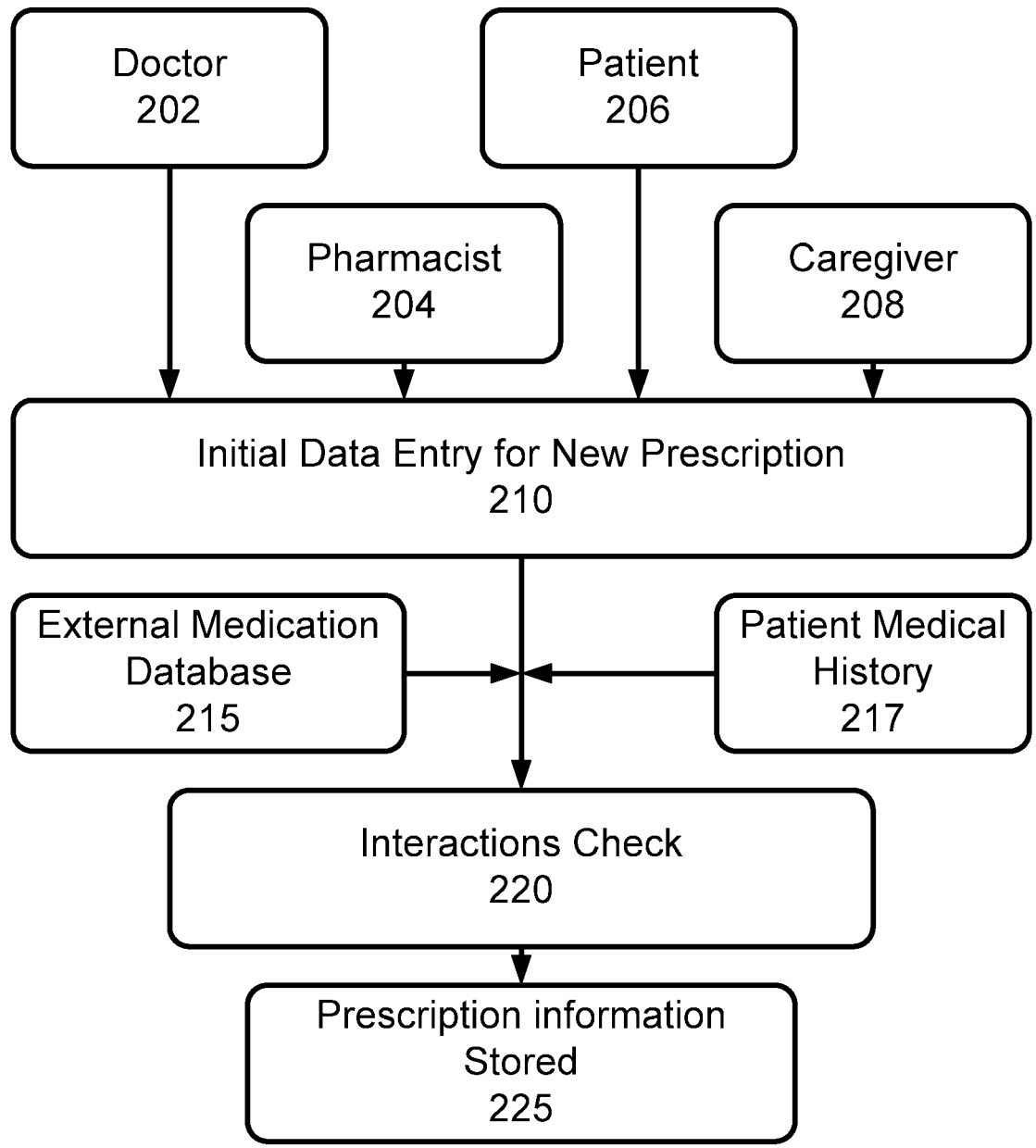
FIG. 2 is a flow chart diagram describing a data entry and prescription assignment process in accordance with an embodiment of the present invention.

Referring next to FIG. 2, a more precise description of the data, medical record and prescription regimen entry will now be described. As is shown in FIG. 2, a number of entities may be able to enter information into a system in accordance with the invention. Such individuals may include a doctor 202, a pharmacist 204, a patient 206 and a caregiver 208. Each of these individuals may be provided with different rights for data entry. For example, a doctor may be provided with the ability to alter patient information, basic medical statistics, and virtually all other medical information included in a database. A pharmacist may be limited to entering information about a particular prescription, including when delivered to a patient, type of pill or medication, dosage size, refill availability, etc. A patient may be limited to providing personal information, and perhaps other relevant information, such as non-prescription medication usage, alcohol consumption, recent symptoms, reaction to use of particular prescription medications and the like. A caregiver may be limited to entering information about patient reactions, times of administration of medication and the like. Such data entry allows for the tracking of an audit trail at this step of administration as well.

Information from each user of the system is combined, where available, and formed into a prescription medication entry 210. In particular, a preferred list of information that may first be provided in accordance with the invention in order to organize the system may comprise a patient name, a user name, if that user is not the patient, and information to be used to provide various alerts, such as a patient email for prescription reminders, contact information for a doctor or caregiver for emergency contact, or the like. In addition, in accordance with the invention, facial images of the patient and other people interacting with the system are stored, or other biometric identifiers, such as fingerprint identification, retinal identification, voice recognition, various provided RFID tags or the like may be employed. Of course, if the patient is a returning patient, such information may be extracted from an existing database stored with another, previous prescription.

Next, a user such as the doctor 202 or the pharmacist 204 may indicate a particular new or recurring prescription medication to be provided to a user. An external medication database 215 is accessed and information regarding such medication is provided, including medication name or names if multiple brand and generic names exist, suggestions for appropriate prescription dosages based upon patient information and the particular version of the medication to be administered, and usage instructions to be provided to the patient, these instructions being modified or supplemented as necessary by the prescribing entity. These usage instructions preferably include detailed administration instructions, including time of day, patient status (i.e. before or after eating, after waking, before sleeping, etc.), precise method of application, and other useful instructions for a user. These instructions also may include video sequences to describe particular details of the medication or administration procedure thereof. They may also comprise alternative versions of instructions so that if a user is unclear regarding a particular set of instructions, an alternative set of instructions may be provided to the patient to aid in adherence to the prescription regimen.

After selection of such a medication, a patient medical history 217 is preferably accessed to provide additional medication and patient information to the prescribing individual. Such information may include, other prescriptions to the patient so that adverse drug interaction may be determined (although if such other prescriptions were implemented in accordance with this invention, such prescriptions will already be known to the system), patient indication of use of non-prescription drugs, patient allergies, patient activity level, past diseases and procedures, and any other information that may be relevant to the prescription of medication.

After all of the information has been entered about the user, and information from the medication and patient database has been accumulated, various medication interactions are checked automatically by the system at step 220. Any dangerous interactions are noted to the prescribing individual, and may preclude entry of the prescription into the system. Other interactions may be noted to the prescribing individual so that the individual may make the patient aware of such situations. These may include, for example a notification that the taking of two medications together may result in stomach pains, so that the patient should take one in the morning and one in the afternoon. Such interactions check will then result in a set of instructions that will be provided to the user, in addition to the more generic medication instructions. Finally, the prescribing individual may review such instructions and supplement them as desired. It should be noted that in accordance with the invention it is contemplated that various instructions provided to a user may comprise hot links to additional audio and visual information that may be provided to a patient to further assist in their adherence to any particular prescribed protocol, or may provide various information regarding the particular medication being taken as will be further described below.

Finally, after all interactions and instructions have been reviewed and approved, the prescription information is stored at step 225. The storing of such a prescription makes the prescription, alerts, help information and the like accessible to a patient and other system users. Furthermore, such completion may also transmit the prescription to a pharmacy or other medication provision facility so that the user is able to simply swing by to pick up the medication or to have the medication delivered to the patient.

Figure 3:
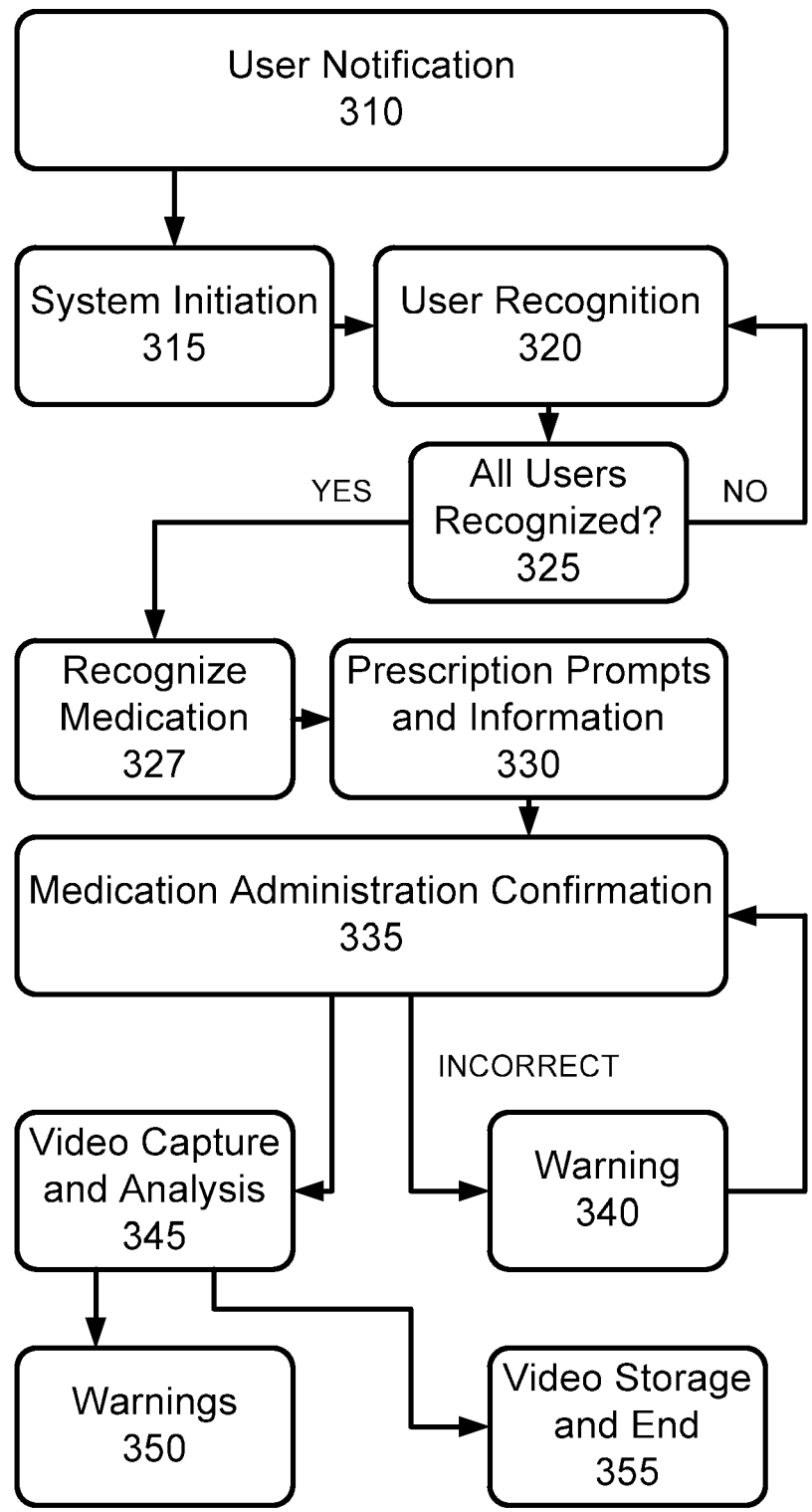
FIG. 3 is a flow chart diagram describing a medical compliance regimen from in accordance with an embodiment of the invention.

Referring next to FIG. 3, a user implementation of the method in accordance with the invention will be described. When a time for receiving or administering a medication is reached, a patient, and any other necessary user may be provided a notification 310 in accordance with notification addresses entered in the system as noted above. Thus, in a home situation, only the patient may receive notification. If there is a home health care provider, such provider may also receive separate independent verification. In the case of hospital or other in-patient care facility, various medical service providers may similarly receive such notification. After notification, or in the absence of such notification, system initiation takes place at 315. In accordance with such system initiation, one or more users are preferably recognized by the system. Therefore, at step 320, a user recognition sequence takes place. In a preferred embodiment, such a user has a still or video image captured of their face, and facial recognition techniques are employed to confirm the identity of the user. Such capture may be performed by fixed camera, mobile camera, mobile communication device such as a cellular phone, or any other appropriate video or image capture device. Alternative recognition techniques, such as retinal, fingerprint, voice or other biometric measurements may be employed, in addition to a more common password query.

At step 325 it is determined whether all necessary users have been recognized and authenticated. In a situation where a nurse, doctor or other caregiver is to administer medication, it may be preferable to have the patient and caregiver to be recognized by the system to further confirm that the appropriate procedure is followed, and to allow the system to keep track of people using the medication so it can track if any one person, for example, is improperly using the medication, as will be evident from the generated audit trail. After step 325, if all users are not recognized, control passes back to step 320 and any additional users are recognized by the system.

Once all users are recognized, control passes to step 327 where the medication to be administered in accordance with the prescribed prescription regimen is confirmed. Thus, a user is prompted to allow a still or video image, text recognition image, or other method of identifying a medication to be captured of the medication bottle or other container, a pill of the medication, or other form of medication, and is also able to determine appropriate quantities, dosage, and any potentially required or dangerous medication combinations. As noted above, if video confirmation is for some reason not available, the user may be prompted by the system to provide audio or other indication of medication and other desired information. This image, video sequence or other received confirmation information is then compared to an image associated with the prescription as noted above in FIG. 2. If the medication is determined to be incorrect, a warning may be provided to the user that the medication is incorrect. The user may then be prompted to choose another medication for imaging.

Alternatively, the invention contemplates a user displaying a number of medications to the image capture apparatus and allowing the apparatus to suggest which medication is correct. Thus, the user may be able to scan a medicine cabinet with such a video imaging apparatus and have the system indicate which is the correct medication. This may prove valuable when sequence of ingesting medication is important, or when two people have similar medications and may have difficulty in distinguishing between medications for each. Once a correct medication has been identified, control passes to step 330.

In step 330 user prompts and other instructions are provided to the patient, and present caregivers, as to how to administer the medication according to the prescription guidelines outlined above. These instructions allow for a user to receive further information or instructions as necessary through asking the system for additional help. Especially in situations where an elaborate scheme may be required, it is contemplated that video samples and instructions may be provided to the user. Further, in accordance with the invention, for complicated administration procedures, it may be possible to set up a two way video conference employing traditional video conferencing, VOIP conferencing, traditional telephone conferencing, or any other appropriate communication system with an expert in such administration so that a caregiver or patient may receive live coaching regarding such administration.

When following such instruction prompts, the actual act of administration is preferably captured as a video sequence at step 335. This captured video sequence may be utilized in accordance with the invention in a number of ways. First, the actions of administration of the medication is reviewed in real time and compared to an ideal or desired video sequence. If a determination is made that the medication is being administered in an incorrect manner, and in a way that may be detrimental to the patient, immediate warnings may be provided at step 340 advising the caregiver or patient to stop administration at once. In the event that such a warning is provided at step 340 indicative of incorrect administration, processing preferably returns to step 335 to capture an additional video sequence to be once again reviewed in real time and compared to an ideal desired video sequence. Furthermore, in extreme cases, a doctor or other caregiver may be notified, or in the most dangerous cases, an ambulance or other emergency personnel may be dispatched to provide immediate care. If video recording is not available, other confirmation methods as noted above may be employed and be subject to automatic confirmation as with the video recorded sequences.

If such immediate care or warning is not required, control then passes to step 345 where the video images are more formally captured and analyzed for various other non-critical issues. The images may be captured and stored locally, being provided to a central server in a batch processing, or images may be captured and sent to the remote server for immediate analysis and storage. Such transmission may take place over a well known Internet connection, wireless connection, or other proprietary communication system. Such analysis may consider suggestions to a caregiver to improve dosage accuracy, reduce pain in administration, or the like. Furthermore, as such video sequences may be available from multiple patients and/or caregivers, the effectiveness of various sets of instructions and the like can be tested and reviewed, and changes thereto made if consistent problems are encountered. This type of study is nearly impossible without the present invention, because in any type of clinical setting, individuals are far more likely to be careful in administration of medication, and therefore not cause errors. However, in accordance with the invention, responses to instructions can be analyzed, and lack of adherence based upon confusing or difficult to follow instructions can be remedied, providing better or more usable instructions, and therefore improving regimen adherence.

In any event, after such analysis, any warnings or suggestions for instruction issues may generate a warning at step 350, suggesting areas of instruction that may be problematic. These video sequences are also stored for longer term analysis if desired at step 355, and processing ends.

It is further contemplated in accordance with the invention that the system and method thereof act as an overall prescription management tool. For example, knowing the prescription and the number of actual times the medication has been administered, the system can order prescriptions to be refilled and sent to the patient. Trends of a patient can be monitored, such as blood pressure or other measurable quantities of the patient, and correlation between such measured quantities and medication administration may be observed, potentially allowing for a more customized solution of medication to be applied to the patient, possible modifying dosage or frequency of administration based upon individual reactions to a particular prescription regimen. Further, insurance administration can be simplified by providing the prescription information directly to the insurance company, and allowing reimbursement for patient costs and other billing issues to be taken care of over a computer network, by phone or the like. Additionally, features of the invention noted above allowing for user interaction and recordation of activities of a user, adverse effects and the like may be incorporated into the system to provide further information for determining alternative instruction sets, modification of medications and the like.

A system provided in accordance with the invention includes imaging technology and hardware, communication hardware, computer systems including storage memory and remote communication via the Internet or other communication network for remote storage and analysis, databases of patient information and medication information sufficient to implement the method as described above.

Therefore, in accordance with the invention, a method and system are provided that allow for the automated administration of medication, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A non-transitory computer readable storage medium, having stored there upon a computer program, the computer program causing a general purpose computer to perform the steps of:
   determining one or more procedures for ingestion of a medication in accordance with a medication prescription regimen;
   identifying one or more predefined movement sequences associated with such procedures;
   providing on a display of a local device one or more instruction prompts instructing a user how to follow the one or more predefined movement sequences, including proper ingestion, of the medication;
   capturing one or more video activity sequences by the local device of a user following the one or more instruction prompts instructing the user to perform the one or more predefined movement sequences;
   storing the captured one or more video activity sequences to a non-transitory computer readable storage medium of the local device;
   comparing the stored one or more video activity sequences in real time to the identified one or more predefined movement sequences by a computer processor associated with the local device;
   determining differences between stored one or more video activity sequences and the identified one or more predefined movement sequences and that the user has failed to properly perform the one or more predefined movement sequences;
   providing one or more further instructions via the display of the local device in real time the one or more further instructions further instructing a user how to properly administer the medication during a current medication administration session in accordance with the one or more predefined movement sequences;
   capturing one or more second video activity sequences by the local device of a user following the one or more further instructions;
   storing the captured one or more second video activity sequences to a non-transitory computer readable storage medium of the local device;
   comparing the stored one or more second video activity sequences in real time to the identified one or more predefined movement sequences by a computer processor associated with the local device; and
   determining there are no differences between the stored one or more second video activity sequences and the identified one or more predefined movement sequences, confirming in real time that the user has properly performed the one or more predefined movement sequences, thus confirming proper medication administration, including ingestion of the medication.

2. The method of claim 1, wherein the medication prescription regimen is provided by a medical professional.

3. The method of claim 1, wherein the medication prescription regimen is retrieved from a medical database.

4. The method of claim 1, wherein the one or more procedures for ingestion of the medication in accordance with the medication prescription regimen are retrieved from a database.

5. The method of claim 4, wherein the determined one or more procedures for ingestion of the medication in accordance with the medication prescription regimen are modified by a medical professional.

6. The method of claim 1, further comprising the steps of:
   retrieving medical history information of a patient to receive the administered medication; and
   confirming that the administered medication is safe for the patient.

7. The method of claim 1, further comprising the steps of:
   before capturing the one or more video activity sequences of the user following the one or more instruction prompts instructing the user to perform the one or more predefined movement sequences, determining the identity of a particular medication to be used in such administration; and
   issuing a warning if it is determined by the computer processor that the determined identity is not the medication associated with the medication prescription regimen.

8. The method of claim 7, wherein the warning includes contact to a medical professional.

9. The method of claim 1, further comprising the steps of:
capturing video activity sequences by the local device of a user following the one or more instruction prompts instructing the user to perform the one or more predefined movement sequences during multiple instances of administration;
transmitting the captured video activity sequences to a remote server location;
further analyzing the captured video activity sequences by a computer processor associated with the remote server location by comparing each of the captured video activity sequences to the identified predefined movement sequences to determine differences therebetween, thereby automatically determining by the computer processor associated with the remote server location that one or more additional activities of the video activity sequence have been improperly performed across one or more of the multiple instances of administration including ingestion; and
providing an analysis of adherence to a particular prescription regimen and the additional activities of the video activity sequence in accordance with the determination of the multiple instances of administration.

10. The method of claim 9, further comprising the step of providing additional instructions to a medication administrator in accordance with the provided analysis.

11. The method of claim 1, wherein the notice further comprises contact to a medical professional.

12. The method of claim 1, further comprising a second notice comprising additional instructions to a medication administrator.

13. A non-transitory computer readable storage medium, having stored there upon a computer program, the computer program causing a general purpose computer associated with a local device to perform the steps of:
authenticating a prescribing medical professional;
receiving information identifying a particular medication prescription regimen from the authenticated medical professional;
determining one or more procedures for ingestion of the medication in accordance with the medication prescription regimen from one or more databases including prescription regimen information in accordance with prescription information provided by the authenticated medical professional;
modifying the one or more procedures, if necessary, by the authenticated medical professional;
identifying one or more predefined movement sequences associated with such determined medication administration procedures;
providing on a display of a local device a set of interactive instructions and associated instruction prompts instructing a user how to follow the one or more predefined movement sequences;
capturing one or more video activity sequences by a video capture device of the local device the user following the one or more instruction prompts displayed on the display to the user instructing the user to perform the one or more predefined movement sequences;
storing the captured one or more video activity sequences including ingestion of the medication by the user to a non-transitory computer readable storage medium of the local device;
comparing by a computer processor of the local device in real time the one or more stored video activity sequences to the identified predefined movement sequences;
determining differences between stored one or more video activity sequences and the identified one or more predefined movement sequences and that the user has failed to properly perform the one or more predefined movement sequences;
providing one or more further interactive instructions to the user via the display of the local device in real time, the one or more further interactive instructions further instructing a user how to properly administer the medication during a current medication administration session in accordance with the one or more predefined movement sequences;
capturing one or more second video activity sequences by the local device of a user following the one or more further instructions;
storing the captured one or more second video activity sequences including ingestion of the medication to a non-transitory computer readable storage medium of the local device;
comparing by the computer processor the stored one or more second video activity sequences in real time to the identified one or more predefined movement sequences by a computer processor associated with the local device; and
determining there are no differences between the stored one or more second video activity sequences and the identified one or more predefined movement sequences, confirming in real time that the user has properly performed the one or more procedures predefined movement sequences, thus confirming proper medication administration, including ingestion of the medication, if no differences are determined.

14. The method of claim 13, further comprising the step of performing a statistical analysis of differences determined in the comparing step.

15. The method of claim 13, wherein the differences determined in the comparing step comprise determining an incorrect medication.

16. The method of claim 13, wherein the differences determined in the comparing step comprise determining an incorrect amount of medication.

17. The method of claim 13, wherein the differences determined in the comparing step comprise determining an incorrect administration procedure.

18. A system for confirming administration of medication, comprising:
a storage device associated with a local device storing prescription administration information associated with an identified medication prescription, a set of instructions in accordance with which the prescription regimen is to be administered including ingestion of the medication, and one or more identified predefined movement sequences associated with such instructions;
a video capture device associated with the local device;
a processor associated with the local system configured to perform the steps of:
capturing video activity sequences with the video capture device of the user following the one or more instruction prompts displayed on the output device instructing the user to perform the one or more predefined movement sequences;
storing the captured video activity sequences to the storage device associated with the local system;
comparing in real time the stored video activity sequences to the identified predefined movement sequences including ingestion of the medication;

determining differences between stored one or more video activity sequences and the identified one or more predefined movement sequences and that the user has failed to properly perform the one or more predefined movement sequences;

providing in real time one or more further instructions, the one or more further instructions further instructing a user how to properly administer the medication during a current medication administration session in accordance with the one or more procedures predefined movement sequences;

capturing second video activity sequences with the video capture device of the user following the one or more further instruction;

storing the second captured video activity sequences to the storage device associated with the local system;

comparing in real time the stored second video activity sequences to the identified predefined movement sequences including ingestion of the medication; and determining there are no differences between the stored second video activity sequences and the identified one or more predefined movement sequences, confirming in real time that the user has properly performed the one or more predefined movement sequences, thus confirming proper medication administration, including ingestion of the medication.

19. The system of claim 18, wherein the information stored on the storage device may be modified by an authenticated medical professional.

20. The system of claim 18, wherein the capture device is further adapted to capture images of a particular medication to allow identification thereof.

21. A non-transitory computer readable storage medium, having stored there upon a computer program, the computer program causing a general purpose computer associated with a local device to perform the steps of:

determining one or more procedures for administering a prescription regimen including ingestion of a medication in accordance with prescription information provided by an authenticated medical professional;

modifying the procedures, if necessary, by the authenticated medical professional;

providing a set of instructions including one or more instruction prompts instructing a user to perform a predefined movement sequence in accordance with which the prescription regimen is to be administered;

identifying one or more predefined visual indicia for determining confirmation of performance of the predefined movement sequence by the user;

providing via an output device of a local device one or more of the one or more instruction prompts instructing a user how to perform the predefined movement sequence, including ingestion of the medication;

capturing appropriate visual indicia by a video capture device associated with the local device of the user following the one or more instruction prompts and performing the predefined movement sequence, including ingestion of the medication;

storing the captured visual indicia to a non-transitory computer readable storage medium of the local device;

comparing in real time the stored visual indicia to the identified predefined movement sequences by a computer processor associated with the local device;

determining differences between the stored visual indicia and the identified predefined movement sequences and that the user has failed to properly perform the one or more predefined movement sequences;

providing one or more further instructions via the output device in real time, the one or more further instructions further instructing the user how to properly administer the medication during a current medication administration session in accordance with the predefined movement sequence by following one or more further instruction prompts in accordance with the one or more further instructions;

capturing second visual indicia by the video capture device associated with the local device of the user following the one or more further instructions;

storing the captured second visual indicia to the non-transitory computer readable storage medium of the local device;

comparing in real time the stored second visual indicia to the identified predefined movement sequences by a computer processor associated with the local device; and determining there are no differences between the stored second visual indicia and the identified predefined movement sequences, confirming that the user has properly performed the predefined movement sequence, thus confirming proper medication administration, including ingestion of the medication.

22. The method of claim 21, wherein the visual indicia for determining confirmation of prescription administration comprises one or more video activity sequences.

23. The method of claim 22, wherein the indicia for determining confirmation of prescription administration comprises an additional alternative method.

24. The method of claim 21, further comprising the steps of:

capturing visual indicia of activity of a patient before medication administration by the video capture device; and providing a reminder to the patient at least in part in accordance with the captured visual indicia before medication administration.

25. The method of claim 21, further comprising the step of capturing visual indicia of activity of a patient by the video capture device before medication administration, wherein the captured visual indicia before medication administration comprises evidence of patient consent.

26. The method of claim 21, further comprising the steps of:

capturing visual indicia of activity of a patient by the video capture device after medication administration;

providing notification to a medical service provider of the activity; and modifying at least one aspect of a prescription regimen in accordance with the captured visual indicia after medication administration.

27. The method of claim 26, wherein the captured visual indicia after medication administration comprises an adverse reaction to the medication.

* * * * *